(12) United States Patent
     Schweizer (10) Patent No.: US 10,709,398 B2
(45) Date of Patent: *Jul. 14, 2020

(54) MEDICAL IMAGING DEVICE HAVING A PAIR OF SMART GLASSES AND METHOD FOR SUPPORTING A PERSON USING A MEDICAL IMAGING DEVICE HAVING A PAIR OF SMART GLASSES

(71) Applicant: Siemens Healthcare GmbH, Erlangen (DE)

(72) Inventor: Hans Schweizer, Plattling (DE)

(73) Assignee: Siemens Healthcare GmbH, Erlangen (DE)

( * ) Notice: Subject to any disclaimer, the term of this patent is extended or adjusted under 35 U.S.C. 154(b) by 247 days.

This patent is subject to a terminal disclaimer.

(21) Appl. No.: 15/957,250

(22) Filed: Apr. 19, 2018

(65) Prior Publication Data
    US 2018/0303446 A1    Oct. 25, 2018

(30) Foreign Application Priority Data
    Apr. 21, 2017  (EP) .................................... 17167535

(51) Int. Cl.
    *A61B 6/00*      (2006.01)
    *G06T 19/00*     (2011.01)
    (Continued)

(52) U.S. Cl.
    CPC ............ *A61B 6/462* (2013.01); *A61B 6/0492* (2013.01); *A61B 6/463* (2013.01); *A61B 6/464* (2013.01);
    (Continued)

(58) Field of Classification Search
    CPC ........... A61B 6/00; A61B 6/04; A61B 6/0492; A61B 6/08; A61B 6/405; A61B 6/46;
    (Continued)

(56) References Cited

U.S. PATENT DOCUMENTS

| 4,196,966 A | 4/1980 | Malis |
| 6,168,278 B1 | 1/2001 | Mukai |

(Continued)

FOREIGN PATENT DOCUMENTS

| DE | 102013201773 A1 | 8/2014 |
| WO | 2005016164 A1 | 2/2005 |

(Continued)

OTHER PUBLICATIONS

Wikipedia, "Smartglasses", https://en.wikipedia.org/w/index.php?title=Smartglasses; Mar. 11, 2017.
(Continued)

*Primary Examiner* — Anastasia Midkiff
(74) *Attorney, Agent, or Firm* — Lempia Summerfield Katz LLC (57) ABSTRACT

A medical imaging device is disclosed herein. The medical imaging device includes a user interface device for displaying information relevant to an imaging process to a user and/or receiving user input relevant to an imaging process and at least one component controllable according to a user command entered using the user interface device, wherein the user interface device includes at least one pair of mixed reality smart glasses.

22 Claims, 7 Drawing Sheets

(51) Int. Cl.
*A61F 9/02* (2006.01)
*G06F 3/01* (2006.01)
*A61B 34/00* (2016.01)
*A61B 6/04* (2006.01)
*G06F 3/0481* (2013.01)
*G06F 3/0484* (2013.01)
*G06F 3/0487* (2013.01)
*A61B 90/50* (2016.01)
*A61B 17/00* (2006.01)
*A61B 90/96* (2016.01)
*A61B 34/10* (2016.01)

(52) U.S. Cl.
CPC .............. *A61B 6/465* (2013.01); *A61B 6/466* (2013.01); *A61B 6/467* (2013.01); *A61B 6/548* (2013.01); *A61B 6/589* (2013.01); *A61B 34/25* (2016.02); *A61F 9/029* (2013.01); *G06F 3/011* (2013.01); *G06F 3/0484* (2013.01); *G06F 3/0487* (2013.01); *G06F 3/04812* (2013.01); *G06F 3/04815* (2013.01); *G06T 19/006* (2013.01); *A61B 90/96* (2016.02); *A61B 2017/00207* (2013.01); *A61B 2017/00212* (2013.01); *A61B 2017/00216* (2013.01); *A61B 2034/107* (2016.02); *A61B 2090/502* (2016.02); *A61B 2560/0487* (2013.01); *G06F 3/016* (2013.01); *G06F 3/04847* (2013.01); *G06T 2200/24* (2013.01)

(58) Field of Classification Search
CPC ......... A61B 6/461; A61B 6/462; A61B 6/463; A61B 6/465; A61B 6/467; A61B 6/469; A61B 6/54; A61B 6/542; A61B 6/547; A61B 6/548; A61B 6/588; A61B 6/589; A61B 2017/00115; A61B 2017/00128; A61B 2017/00199; A61B 2017/00207; A61B 2017/00212; A61B 2017/00216; A61B 2017/00221; A61B 34/10; A61B 34/20; A61B 34/25; A61B 90/36; A61B 90/37; A61B 2034/107; A61B 2034/2046; A61B 2034/2055; A61B 2090/364; A61B 2090/365; A61B 2090/368; A61B 2090/376; A61B 2090/3762; A61B 2090/3764; A61B 2560/0487; A61F 9/02; A61F 9/022; A61F 9/025; A61F 9/029; G06F 3/011; G06F 3/012; G06F 3/013; G06F 3/014; G06F 3/016; G06F 3/017; G06F 3/048; G06F 3/0484; G06F 3/04842; G06F 3/04845; G06F 3/04847; G06F 3/0485; G06F 3/04855; G06F 3/0486; G06F 3/0487; G06F 3/0488; G06F 3/04886; G06T 19/006; G06T 2200/24; G06T 2210/41; H04N 13/344

See application file for complete search history.

(56) References Cited

U.S. PATENT DOCUMENTS

| | | | |
|---|---|---|---|
| 6,824,265 | B1 | 11/2004 | Harper |
| 2006/0187192 | A1 | 8/2006 | Kagermeier et al. |
| 2007/0073137 | A1 | 3/2007 | Schoenefeld |
| 2014/0081659 | A1 | 3/2014 | Nawana et al. |
| 2016/0307001 | A1* | 10/2016 | Dow ................. G06F 21/83 |
| 2016/0324580 | A1 | 11/2016 | Esterberg |
| 2018/0228556 | A1* | 8/2018 | Schweizer ........... A61B 6/464 |

FOREIGN PATENT DOCUMENTS

| | | |
|---|---|---|
| WO | 2005066744 A1 | 7/2005 |
| WO | 2011085815 A1 | 7/2011 |
| WO | 2013144752 A1 | 10/2013 |
| WO | 2016133644 A1 | 8/2016 |

OTHER PUBLICATIONS

European Search Report for related European Patent Application, dated Nov. 2, 2017.

European Search Report for related European Patent Application, dated Jan. 15, 2018.

\* cited by examiner

MEDICAL IMAGING DEVICE HAVING A PAIR OF SMART GLASSES AND METHOD FOR SUPPORTING A PERSON USING A MEDICAL IMAGING DEVICE HAVING A PAIR OF SMART GLASSES

The application claims the benefit of European Patent Application No. EP 17167535.8, filed Apr. 21, 2017, which is hereby incorporated by reference in its entirety.

TECHNICAL FIELD

The disclosure relates to a medical imaging device, including a user interface device for displaying information relevant to an imaging process to a user and/or receiving user input relevant to an imaging process and at least one component controllable according to a user command entered using the user interface device. The disclosure also relates to a method for supporting a person during an imaging process and/or a surgical intervention under image surveillance using such a medical imaging device.

BACKGROUND

Current medical imaging devices offer a great number of functions and accordingly a great number of complex operating elements. For example, concrete embodiments of imaging processes and thus the imaging parameters vary greatly depending on the area imaged and the diagnostic goal. While imaging processes are sometimes hard to operate, this problem grows more severe if the medical imaging device is used in sterile environments, (e.g., during a surgical intervention). For example, medical imaging devices having a c-arm and a mobile carrier for the c-arm may be used as interventional modalities. In such an environment, an operating device has to be provided which on the one hand allows ergonomic use of the complex functions, on the other hand fulfils the requirements for a sterile operation.

In this context, it has been proposed to cover operating elements of user interface devices, which may be sterilely operated, with a sterile, transparent foil, sheet or drape. This measure is required because the provided operating elements may not suitable for sterilization, (e.g., steam sterilization), as they contain electronic components, (e.g., displays). Therefore, they do not fulfil the requirements regarding hygiene and sterility. A disadvantage of using sterile covers is the reduction of operating ergonomics and required additional, time-consuming steps while preparing the surgery or imaging process, because a covering foil which is complicated to handle has to be wrapped around the relevant operating elements.

It should be noted that operating elements of user interface devices in known medical imaging devices may be provided at multiple different locations on the device. For example, an x-ray imaging device may include buttons at the housing of the x-ray detector and touchscreens for controlling additional functions, which are located on a separate display unit or display trolley. An additional disadvantage of the current state of the art is thus that a user working at a certain location relative to the medical imaging device may not have access to all functions and operating options. Regarding a medical imaging device having a c-arm, it is possible that a user position close to the c-arm does not allow access to all functions related to the c-arm without moving. Additionally, a user, who may be required to work in a sterile environment, may have to leave the sterile area to operate these functions. A further problem is that some displays may not be adequately positioned such that the user may see all information relevant to the current state of the imaging process.

A major problem of today's medical imaging devices is, in summary, that requirements for sterility reduce ergonomics, operating elements of user interface devices are spread over components of the medical imaging device and information is not always accessible when required.

SUMMARY AND DESCRIPTION

It is an object of the current disclosure to provide a medical imaging device and a support method which allow an improved, intuitive operation of the medical imaging device while fulfilling requirements regarding sterility.

The scope of the present disclosure is defined solely by the appended claims and is not affected to any degree by the statements within this description. The present embodiments may obviate one or more of the drawbacks or limitations in the related art.

A medical imaging device, including a user interface device for displaying information relevant to an imaging process to a user and/or receiving user input relevant to an imaging process and at least one component controllable according to a user command entered using the user interface device, also has at least one pair of mixed reality smart glasses as part of the user interface device.

The mixed reality smart glasses are configured to display at least part of the imaging process relevant information and/or to receive at least part of the imaging process relevant user input. Such mixed reality smart glasses have already been proposed in the state of the art and may also be termed augmented reality smart glasses. Such smart glasses are, for example, available under the trade mark "HoloLens" (Microsoft) or "MetaVision". These devices may be worn covering the eyes of the user. An augmented reality is provided by projecting additional computer-generated information into the field of view of the user. Such a pair of smart glasses may include a plurality of sensors, in particular, three-dimensional (3D) cameras and/or RGB cameras and/or at least one movement sensor for tracking the head wearing the smart glasses. The smart glasses additionally include projection units for each eye, providing stereoscopic view, a control device, and/or a speaker/microphone. The control unit of the smart glasses may be configured to map augmented reality objects to the in particular sensed environment geometry and to display perspectively correct and stereoscopic graphical elements (e.g., augmented reality objects) using the projection units. The control unit may further be configured to detect and identify operating gestures performed by the user. It is noted that the control unit or at least parts of the control unit may also be located externally to the smart glasses, for example, inside a computing device. This is also possible for sensors. For example, an "inside-out" tracking of the smart glasses may be supported or replaced by external tracking devices (e.g., "outside-in" tracking), for example, by using externally trackable markers on the smart glasses. This may improve accuracy of tracking.

It has also been proposed to have more than one user wearing such smart glasses. These pairs of smart glasses may communicate directly or indirectly, allowing to match the augmented realties created for each user. Thus, all users see the same objects/graphical elements, configured to their respective point of view.

The disclosure proposes to use such a pair of smart glasses to improve imaging processes in view of operation of the medical imaging device as well as informing the user. Operating elements which may be difficult or even impossible to sterilize may be omitted, because they may be replaced by virtual operating elements projected into the field of view of the user at locations related to their purpose and function. Such virtual operating elements need not be sterilized at all and may be configured to suit the needs of the individual users. The workflow may be improved because all operating elements required in certain situations may be placed within reach of the user. The overall workflow of the imaging process is improved.

This also applies to the presentation of information as graphical elements, (e.g., information elements), in particular, regarding information with a certain spatial relatedness, (e.g., imaging geometries), radiation exposures and the like. Information may be displayed proximate or even on the components it relates to, such that an intuitive understanding is facilitated.

One field of application relates to x-ray imaging devices, such that in one embodiment, the medical imaging device is an x-ray device (e.g., a mobile x-ray device), in particular configured for intraprocedural imaging. Also, at least one of the components is or constitutes an imaging assembly including at least an x-ray source, an x-ray detector, and, e.g., a c-arm. Such mobile c-arm x-ray devices are complex to operate because many degrees of freedom exist, in particular regarding the imaging geometry. Certain components, (e.g., at least the x-ray source, detector, and/or the c-arm), are moveable to define imaging geometries for the imaging process. In this context, user commands may define movement of such components. The disclosure may also be applied to stationary c-arms. Although most of the concrete embodiments mentioned in this description may relate to x-ray medical imaging devices, the disclosure is also applicable to other medical imaging modalities, such as ultrasound or magnetic resonance imaging.

It is noted that user commands may include choosing certain imaging parameters defining the imaging process, in particular imaging parameters relating to imaging geometry, as will be further discussed below.

The smart glasses may be configured to project at least one information element relating to the imaging process into the field of view of a user wearing the smart glasses. In particular, if an information element relates to a certain component or spatial position, the information element may be displayed close to or on the component/position. Thus, information may be displayed intuitively in its context.

In a concrete embodiment, at least one of the at least one information element includes a field of view of the imaging device, displayed at its actual location. In an x-ray device, the field of view may include a radiation field. In such a case, the information element or an additional information element may include a central beam in case of a cone-beam or fan-beam geometry.

Displaying the field of view as an information element is possible because components of the medical imaging device defining the field of view may be localized in many different ways, allowing the derivation of knowledge on the position of the field of view of the medical imaging device in space. If a control device of the medical imaging device keeps track of the positions of the relevant components, the corresponding coordinate system may be registered to a coordinate system of the smart glasses such that the location of the field of view is known to projection units and the control unit in the smart glasses. However, it is also or additionally possible to locate components of the medical imaging device using sensors of the smart glasses, in particular optical sensors like cameras, as further described below.

In an especially advantageous embodiment, the smart glasses are configured to project at least one interactive virtual operating element into the field of view of a user wearing the smart glasses, wherein a control unit of the smart glasses is configured to derive at least one user command from interactions of the user with the virtual operating element as detected by at least one sensor of the smart glasses. Graphical elements of the smart glasses projected into the field of view of the user may thus include interactive virtual operating elements, as already mentioned above, while sensors of the smart glasses may detect interactions of the user with the virtual operating element. These interactions may be analyzed, for example, using gesture detection algorithms as known from the state of the art, such that user commands may be derived. In one embodiment, the virtual operating element may include a push button, wherein the interaction may be a pushing/pressing of the virtual operating element. If such a gesture is detected from corresponding sensor data, a user command associated with pushing the push button of the virtual operating element is detected and implemented.

Information elements and virtual operating elements may also be combined, for example, in such a manner that the information element is or includes a virtual operating element. In certain embodiments, it is possible to interact with information elements, (e.g., a central beam), using the information element as a virtual operating element, providing an intuitive way to operate the medical imaging device.

As has already been described, the virtual operating element and/or the information element may be displayed in a predefined geometrical relationship to at least one component of the medical imaging device. The control unit of the smart glasses may for this purpose be configured to identify and locate the component based on sensor data of the smart glasses sensors, for example, by using pattern recognition algorithms and/or other imaging processing algorithms. To aid this evaluation of sensor data or as an alternative, the medical imaging device may also include optical markers and/or barcodes attached to these components. In another example, additionally or alternatively, location information regarding components may be provided by a control device of the medical imaging device tracking these components, wherein the coordinate systems in which the components are tracked, and the coordinate systems of the smart glasses are co-registered.

In a concrete example, if the medical imaging device is an x-ray device having a c-arm, the c-arm may be easily detected in sensor data, (e.g., of a 3D-camera), by using pattern recognition techniques. To support this identification and localization of the c-arm and the x-ray source and the x-ray detector mounted to the c-arm, the c-arm and/or other components, (e.g., the x-ray source and/or the x-ray detector), may be provided with optical markers and/or barcodes, (e.g., QR codes). Once the position of the x-ray source and the x-ray detector are known, the current field of view may be calculated and projected into the field of view of the user of the smart glasses as an information element. For example, in a fan-beam geometry, the radiation field may be shown as a frustum of pyramid between the x-ray source and the x-ray detector. The central beam may also be visualized, for example, as a line. Even if these information elements were not interactive, the display is advantageous because the invisible x-rays are made visible using the virtual projection.

The positioning of the c-arm relative to a patient is facilitated such that, for example, positioning lasers and the like may be omitted.

The geometric base model of the field of view of the medical imaging device may be enhanced adding additional information, (e.g., areas of direct radiation and scattered radiation and/or radiation intensities), such that this additional information may also be provided to the user. For example, the frustum of a pyramid representing the field of view of the medical imaging device may be projected into the field of view of the user using a color gradient to display radiation intensity. In an embodiment, areas of scattered radiation may be shown which is expedient for the user to avoid unnecessary radiation exposures. It is also possible to color the information element according to a radiation dose set by the user. It should be noted at this point that when calculating the field of view, imaging parameters of optical elements affecting the field of view, (e.g., collimators and/or diaphragms), may be taken into account.

In the example of an x-ray device, other possible information elements may be considered. For example, information elements may be projected/overlaid on the c-arm and/or other components, for example, components of a cooling device for the x-ray source, for example, the current temperature of the x-ray source which is relevant in longer radiation sequences. For example, a tank holding a cooling medium for the x-ray source may be colored according to the temperature, such that a warm or hot tank may appear in red.

In the example of an x-ray device having a c-arm, certain embodiments exist in which information elements are also used as interactive virtual operating elements. For example, the central beam may be used as a virtual operating element, such that by grabbing the central beam and moving, (e.g., rotating), the central beam the user may enter user commands, resulting in movement of the c-arm to establish the newly chosen position and/or direction of the central beam. When using the central beam as a virtual handle, the central beam may be repositioned by rotating the c-arm and/or moving the c-arm in a horizontal plane and/or vertically lowering or raising the c-arm. Alternatively, or additionally, the field of view may also be adjusted by using a pointing gesture, for example, pointing to a new region of interest and/or pointing into a direction which may be used as direction select for the central beam. A new position of the c-arm is calculated such that these directions match and/or the region of interest is included in a new field of view of the medical imaging device.

In such an embodiment, it is also possible to control imaging parameters of optical elements by interacting with information elements as virtual operating elements. For example, the aperture of a radiation diaphragm or collimator may be controlled using a two-finger gesture, wherein the distance between the fingers may define the aperture of the diaphragm or collimator.

It is of course also possible to add additional interactive virtual operating elements to the information elements. For example, additional virtual selection buttons may be projected into the field of view as part of the field of view information element or additional graphical elements. By virtually pushing these selection buttons, the user may disable certain movement axes or chose a special type of movement which is to be effected by interacting with the central beam as further virtual operating element. For example, an isocentric orbital rotation of the c-arm or a linear lateral movement along the patient table may be chosen.

In an embodiment, the user interface further includes at least one operating aid having at least one display surface, wherein the control unit is configured to identify and locate the display surface and project at least one of the at least one virtual operating element to appear on the display surface for the user wearing the smart glasses. It has been found that it is difficult for many users to interact with operating elements only virtually present without being bound to any physical component or object. Thus, it is proposed to use an operating aid which has a display surface and may be used as physical object associated with virtual operating elements, providing an actually touchable, but virtual operating element. Multiple interactive virtual operating elements may be projected to appear on such a display surface, in particular, combined with information elements.

It is noted that, while, of course, virtual operating elements may also be or include information elements, it is also possible to project pure information elements into the field of view of the user such that they appear on the display surface. For example, a currently chosen radiation dose may be displayed as information element adjacent to virtual operating elements allowing to increase or decrease the dose.

Also concerning the use of operating aids, the control unit may be configured to calculate respective perspective views of the virtual operating elements depending on the viewing angle of the person, as in principle known from the art.

The operating aid may be provided in different geometrical forms and variants but may be a plate, which may be made from (e.g., steam-) sterilizable plastic, ceramics, glass, or the like. Such a plate may also be termed passive projection plate because active electronics realizing operating elements may be omitted. The operating aid will in most cases, at least regarding the display surface be white, but also different colors, which fit into the imaging or surgery environment, are possible. The operating aid has a sterilizable surface, (e.g., made of plastic). Thus, the operating aid may be sterilized without any problematic interactions with electronics, wherein, in particular, steam sterilization is envisioned.

However, it should be noted that single-use solutions are also conceivable. In such an embodiment, the operating aid may be supplied in a sterile packaging and disposed of by the user after the imaging process.

Further, the operating aid may have at least one fixation device, (in particular, a magnetic fixation device and/or a fixation device), configured to interact with a magnetic fixation device and/or a standardized fixation device of the medical imaging device, for reversibly fixing the operating aid to another component of the medical imaging device. In an embodiment, the operating aid may have a magnetic backside, such that it may be fastened to suitable, magnetic, or metallic surfaces without having to use tools. Alternatively, or additionally, the operating aid may include a universal interface used for mounting the operating aid to established, standardized fixation device in particular used in surgery, for example, a surgical rail (e.g., accessory rail) of a patient table. In other embodiments, it is also possible to use tailored mechanism including a fixation device of the operating aid and a mating fixation device of a component of the medical imaging device to which the operating aid may be mounted.

In an embodiment, a repositioning device for moving the operating aid between at least one usage position and at least one storage position may be provided. The repositioning device may be a pivot, such that the operating aid may be swung into the storage position when not needed.

In an embodiment, multiple virtual operating elements, in particular, combined with information elements, may be projected onto the display surface to create the illusion of a graphical user interface. While virtual operating elements may include push buttons and sliders, these are particularly useful in such a virtual user interface. If, for example, a plate is used as operating aid, such a virtual graphical user interface may act as a virtual touchscreen.

In many cases, it is advantageous to use multiple operating aids to display virtual operating elements and possibly information elements on the respective display surfaces. In particular, in such an embodiment, the operating aid may include at least one marker and/or barcode including or associated with identification information of the operating aid. The control unit may thus identify operating aids and, in particular, properties of operating aids, (e.g., the size of the display surface and the like). The control unit may further be configured to choose the content projected onto the display surface depending on the identification information and/or properties of the operating aid, for example, the size of the display surface. Markers and/or barcodes, (e.g., QR codes), allow an unambiguous detection of the operating aid also under difficult circumstances. Optical markers and/or barcodes may also facilitate the detection of the spatial orientation of the operating aid. In particular, barcodes or other markers carrying identification information may also be used when more than one operating aid is used simultaneously. The content projected onto the display surface, (in particular, of a virtual graphical user interface), may be selected depending on the type of operating aid and/or other properties of the operating aid.

In an embodiment, when using different operating aids, all may have different sets of operating elements projected onto their display surfaces, in particular different virtual graphical user interfaces. If, for example, two plates are used as operating aids having differently sized display surfaces, the larger display surface may be used to project the complete virtual graphical user interface, whereas a reduced graphical user interface is projected onto the smaller display surface.

In an especially advantageous embodiment, the operating aid has at least one tactile surface structure corresponding to a virtual operating element displayed at the position of the surface structure. Such a tactile surface structure may include protrusions, recesses, ripples and/or the like. In particular, in cases of designing graphical user interfaces to be projected onto display surfaces in a manner that certain operating elements are displayed at predetermined grid positions, it is advantageous to have tactile surface structures at locations where virtual operating elements are displayed. This allows the user to "feel" the operating elements, providing a more intuitive operation.

The operating aid and/or a component to which the operating aid is mounted may include at least one pressure switch to indicate at least a local pressing of and/or a capacitive sensor detecting at least local interaction with the operating aid, wherein user commands are grouped into safety relevant commands and other commands and the user interface device is configured to interpret an interaction with a virtual operating element projected onto the display surface, which interaction corresponds to a safety relevant command, only as the corresponding user command if the pressure switch and/or capacitive switch indicates pressing of and/or interaction with the operating aid. In this advantageous embodiment, it is possible to measure actuation of virtual operating elements at least in cases in which a safety relevant function is to be operated. Examples for such safety related user commands include those concerning movement of components of the medical imaging device, for example, movement of a c-arm. An additional pressure switch may thus be included into the operating aid or in the area of attachment of the operating aid to a component of the medical imaging system. The pressure switch generates a hardware signal additional to a detected interaction when the user pushes the operating aid mechanically. Only if both the detected interaction and the hardware signal, acting as confirmation signal, are present, the relevant function/user command is accepted. In this manner, the disclosure also allows operating functions relevant for security/safety. As an alternative to a pressure switch, also usage of a capacitive sensor is thinkable, detecting the changes in electrical fields upon user interaction.

It is, of course, also possible that the user interface device includes a confirmation aid, for example, in the form of a hand or foot operated switch, to generate a confirmation signal required to enter a safety relevant command. Such a confirmation aid may also be used in embodiments where no operating aid is present. If, for example, a virtual operating element like the central beam of a radiation field is used, the interaction with which produces movement of components, (e.g., of a c-arm), a confirmation aid, (e.g., a foot or hand operated switch), may have to be actuated additionally to allow the safety relevant user command or, in other words, unlock movement of the corresponding components of the medical imaging device.

A hand-operated confirmation aid may be a sterilizable or sterilely wrapped cylinder having at least one push button. Confirmation aids may communicate wirelessly with other components, (e.g., the control unit of the smart glasses).

Regarding operating aids, numerous possibilities exist where operating aids may be mounted. For example, the operating aid may be mounted on the backside of a display trolley, on the patient table, or the housing of the detector. Projection aids may also be mounted to the wall or ceiling of an imaging or surgery room, for example, using suitable mounts or holders. Ceiling-mounted operating aids may be used to mainly or purely display information elements.

In embodiments, the present disclosure also allows to aid the user in operating virtual operating elements not bound to physical, tangible objects, for example, the above-mentioned central beam. Additionally, the disclosure may facilitate the input of more complicated user commands, such as symbols, in such embodiments. To achieve this, in certain embodiments, the user interface device further includes at least one interaction aid to be carried by the user and used for interacting with the virtual operating element. Such an interaction aid may include a passive, sterile pen associated with at least one display surface to facilitate certain interactions with operating elements, for example, drawing interactions. The pen as such does not need to have any electronic components or the like and is only used to facilitate user input, wherein the interaction aid may be detectable by sensors of the smart glasses. The interaction aid may also include a stick or other direction defining aid. For example, an elongated interaction aid may be used as a handle and/or a direction defining aid. In the above-mentioned example of a central beam as a virtual operating element, an elongated interaction aid may allow tactile grabbing of the virtual projection and a clearer definition of directions.

The interaction aid may also act as confirmation aid, in this case including at least one confirmation switch to generate a confirmation signal required to enter a safety relevant command as user command. For example, an elongated interaction aid may have a push button-activated confirmation switch at one end of its cylindrical body. Any remarks relating to the pressure switch/capacitive sensor of the operating aid also apply here.

In an embodiment, the operating aid and/or the interaction aid include a haptic feedback device generating feedback signals on user input, in particular user commands. Such a haptic feedback device may also be provided in a confirmation aid. The haptic feedback mechanism may communicate wirelessly with a control device of the user interface device or the medical imaging device in general. A haptic feedback device allows confirmation of detected user commands and/or confirmation of execution of user commands. For example, the haptic feedback device, which advantageously does not compromise sterilizability of the respective aid, may vibrate to confirm user commands or the execution. Multiple different haptic signals associated with different user commands and/or states of detection may be used.

All mentioned aids may be sterilizable, in particular, steam sterilizable.

In an advantageous embodiment, the smart glasses may include a holder for at least one vision-related surgery or imaging accessory. It is thus proposed to provide the mixed reality smart glasses with a holder for certain accessories may be used while imaging or performing surgery. The holder may include a mounting bracket and/or may be mounted to or adjacent to a visor of the smart glasses.

The holder may be configured for removably receiving at least one accessory and/or includes at least one positioning device for moving the accessory between at least one usage position in the field of view a user and/or influencing the field of view of the user and a non-usage position. In the case of removably mounting the accessory, e.g., the holder includes a quick fastener, such as a magnetic quick fastener. The positioning device may include a pivot and/or a motor for automatically moving the accessory, in particular in response to user input using the user interface device, for example, a gesture. If a mounting bracket is used as a holder, it may be hinged such that a transparent plane may be added in the field of view of the user as required. While it is possible to manually actuate the positioning device and/or the holder, respectively, the positioning device may also include an actuation unit, (e.g., a motor), to allow automatic positioning of the accessory. Automatic positioning may be initiated by a user command detected by sensors of the smart glasses.

In an embodiment, more than one accessory is fastened to the holder. Actuating the positioning device may then remove an accessory from the field of view of the user or a position influencing it and/or exchange accessories.

In an embodiment, if the smart glasses have a control unit configured to project graphical elements, (e.g., virtual operating elements and/or information elements), into the field of view of the user wearing the smart glasses, the smart glasses may include at least one sensor configured to measure accessory sensor data describing the presence and/or position and/or type of an accessory, wherein the control unit is configured to control the display of graphical elements depending on the accessory sensor data. The sensors used may also be sensors which are used for detecting interactions of the user with virtual operating elements or may include additional sensors. It may thus be detected if an accessory is mounted and inside and/or influencing the field of view of the user. Control of the smart glasses may then be configured to the current situation regarding accessories. For example, projection of graphical elements may be deactivated if an accessory, (e.g., including a magnifying lens), is present in the field of view of the user. In an embodiment, the accessory may include a storage element, (e.g., an RFID or NFC tag), configured to be read out by the sensor acquiring the accessory sensor data. Additional accessory information, (e.g., including the type of accessory), may be stored in the storage element. Using such a storage element, additional information regarding the accessory may be obtained. Using this information, the projection of graphical elements may be configured to the accessory regarding content and position of the graphical elements. For example, additional operating elements relating to the accessory may be added and/or graphical elements concealed by the accessory may be moved to different positions.

The at least one accessory may be a magnifying accessory including at least one magnifying lens, a filter accessory, a head lamp, a protection accessory, in particular for x-ray protection and/or cataract prevention, splash protection, and/or laser protection, and the like.

An accessory requiring electrical energy may be supplied via the holder from a battery of the smart glasses and/or an external interface of the smart glasses, (e.g., a micro USB interface). If the smart glasses have an electrical interface, (e.g., micro USB or an inductive charging interface), and/or an energy source, (e.g., a battery), the holder (in case of a positioning device having a motor) and/or the accessory (if it requires energy) may be supplied with electrical energy using these functional units. It is, however, also possible to have an energy source in the accessory itself.

It should be noted that at least one functional element of a known accessory may also be integrated into the smart glasses, (e.g., into the visor). For example, the smart glasses may include an x-ray protective coating on the visor or an x-ray protective material in the visor.

A method for supporting a person during an imaging process and/or a surgical intervention under image surveillance includes using at least a pair of mixed reality smart glasses of a medical imaging device. The smart glasses are used for displaying information relevant to an imaging process to a user and/or receiving user input relevant to an imaging process. All features and remarks regarding the medical imaging device also apply to the method.

DETAILED DESCRIPTION

Further details and advantages of the present disclosure may be taken from the following description of certain embodiments in conjunction with the drawings, in which.

DETAILED DESCRIPTION

Figure 1:
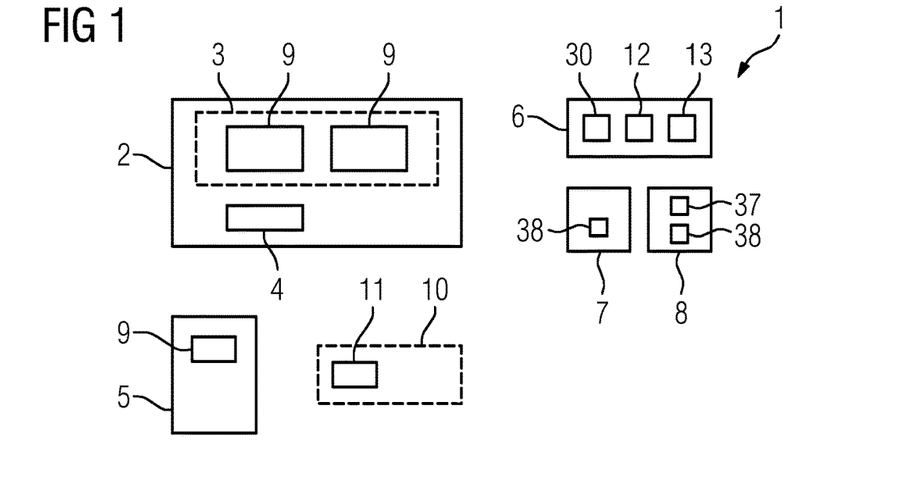
FIG. 1 depicts an example drawing of components of a medical imaging device.

FIG. 1 is a drawing showing principal components of a medical imaging device 1. The imaging device 1 includes an imaging apparatus 2. The imaging apparatus 2 in turn does include an image acquisition unit 3 (as imaging assembly) and a patient table 4. Further principal components of the medical imaging device 1 include a display trolley 5, which is mobile and on which multiple displays are mounted. The display trolley 5 is part of a user interface device for displaying information and receiving user input relating to imaging processes. The user interface device further includes at least one pair of mixed reality smart glasses 6, an optional confirmation aid 7, an optional interaction aid 8, and multiple operating aids 9 in the form of plates or boards which are mounted to various components of the medical imaging device, as further explained below. The medical imaging device 1 is controlled by a distributed control device 10, which also includes a control unit 11 for the smart glasses 6, which may at least in part be integrated into the smart glasses 6.

The mixed reality smart glasses 6 may be of any type already known, (e.g., "HoloLens" by "Microsoft"). The smart glasses 6 in this case include projection units 30 for both eyes, sensors 12 for acquiring sensor data regarding the environment, the user of the smart glasses, movement of the smart glasses 6 for tracking purposes and/or further information, and optionally acoustic equipment 13 including a speaker and a microphone. The sensors 12 may include at least one 3D camera.

The control unit 11 is configured to map augmented reality objects, in this case graphical elements including information elements and interactive virtual operating elements, to the environment geometry measured using sensors 12, so that the augmented reality objects may be projected accurately and using the correct perspective by the projection units 30. The control unit 11 further evaluates sensor data of the sensors 12 to detect interaction of the user with virtual operating elements and/or other gestures which may be interpreted as user commands. As such, smart glasses are in principle already known in the state of the art, they shall not be discussed further.

Figure 2:
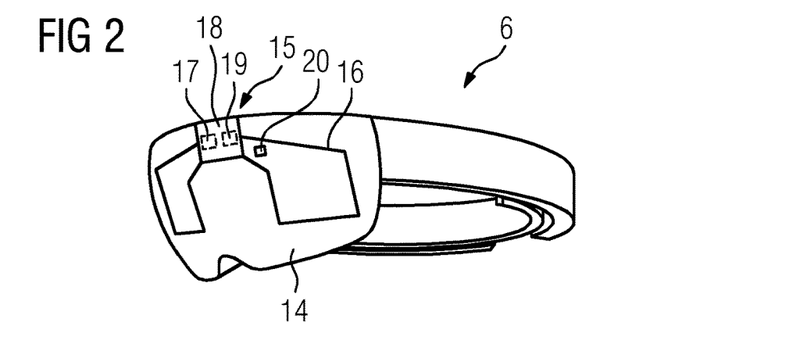
FIG. 2 depicts a first view of an exemplary pair of smart glasses.
Figure 3:
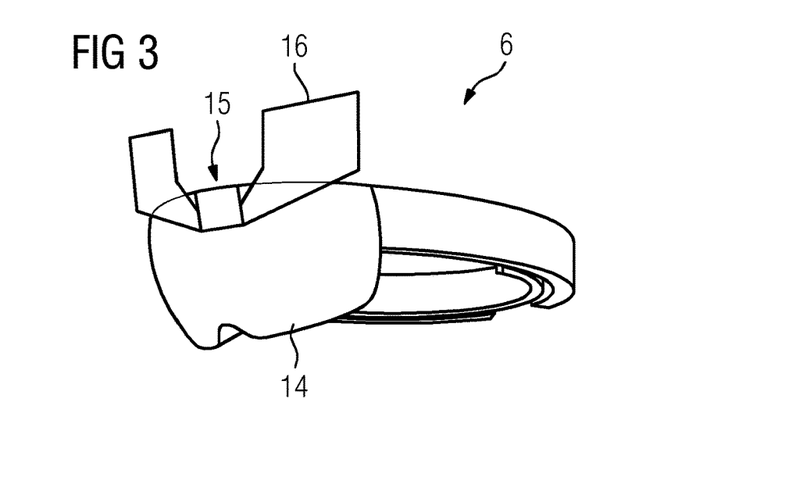
FIG. 3 depicts a second view of the smart glasses.

FIG. 2 depicts a perspective view of the smart glasses 6. The smart glasses 6 include a visor 14 through which the user may see the environment in his field of view and which is also used as projection surface for the projection units 30. The smart glasses 6 further include a holder 15 in the form of a mounting bracket, which holds an accessory 16. The accessory 16, which in this case may be a magnifying accessory, a filter accessory and/or a protection accessory, is mounted removably to the holder 15 using a magnetic quick fastener 18. A positioning device 17 facilitates pivoting the holder 15, allowing the accessory 16 to be swung out of the field of view of the user as shown in FIG. 3.

The positioning device 17 may include a motor 18 allowing automatic pivoting of the accessory 16 out of the field of view of the user and into the field of view of the user. This automatic movement may be effected after detecting a user command, in particular a gesture and/or voice command, by evaluating sensor data of the sensors 12.

It is noted that the smart glasses 6 may additionally or alternatively include further holder, e.g., a holder for a head lamp as accessory.

The smart glasses 6 include at least one sensor able to acquire information on the position and/or type of the accessory 16, which may be one of the sensors 12 or an additional sensor. Using such a sensor, accessory sensor data may be measured and evaluated to derive accessory information on the position and/or type of the accessory 16. The accessory 16 may include a storage element 20, (e.g., an RFID tag), in which accessory information may be stored to be read out by the sensor.

Depending on the accessory information, the control unit 11 may control the projection of graphical elements, for example, deactivate graphical elements in areas of the field of view covered by the accessory 16 or providing different information elements and/or virtual operating elements related and/or configured to the accessory 16.

In this embodiment, the medical imaging apparatus 1 is an x-ray imaging apparatus. The visor 14 includes x-ray protection material.

Figure 4:
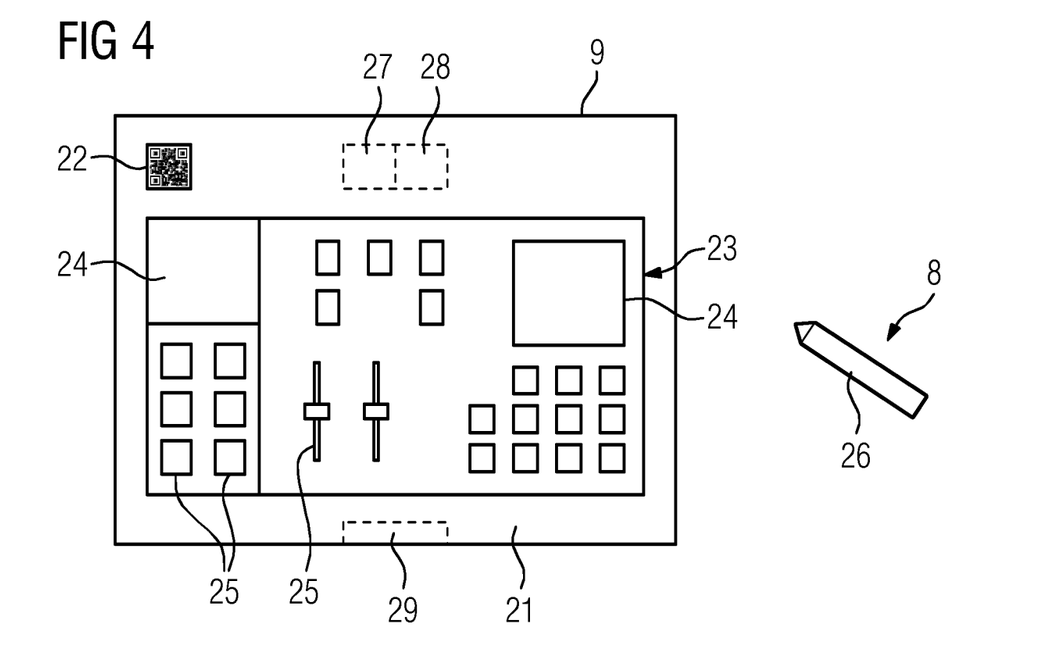
FIG. 4 depicts an example of an operating aid with graphical elements projected thereon.

The operating aids 9 already indicated in FIG. 1 are also used in conjunction with the smart glasses 6. FIG. 4 depicts a plate-shaped operating aid 9 having a display surface 21 on which graphical elements also indicated in FIG. 4 are projected using the projection units 30 of the smart glasses 6. The operating aid 9 also includes at least one barcode 22, in this case a QR code, as optical marker. These optical markers serve to identify the operating aid 9 using the sensors 12 of the smart glasses 6, in this process gaining more information on the size and location of the display surface 21. The optical markers/bar codes allow to accurately measure the position and orientation of optical aids 9 using the sensors 12. The operating aid 9 is made from white, sterilizable material, such as plastics, ceramics, metal and/or glass, and may include surface structures in the area of the display surface 21 where operating elements appear by projection using the smart glasses 6. These surface structures are not shown in FIG. 4.

Instead, a virtual graphical user interface 23 including information elements 24 and interactive virtual operating elements 25 as well as combinations thereof is indicated. The graphical elements 24, 25 forming the virtual graphical user interface 23 are projected by smart glasses 6 into the field of the user such that they appear on the display surface 21, the operating elements 25 spatially coinciding with the mentioned surface structures. Interaction of the user with the operating elements 25 may be detected by the sensors 12 and user commands may be derived.

FIG. 4 also depicts an interaction aid 8 in form of a plastic or metal pen 26 associated with the operating aid 9. The interaction aid (e.g., pen 26) may be used to draw complicated symbols and thus allow more complicated gestures/interactions with virtual operating elements 25.

Operating aid 9 has at least one fixation device 27, 28, wherein in this embodiment the fixation device 27 is a magnetic fixation device facilitating mounting the operating aid 9 to magnetic surfaces, the fixation device 28 is a standardized universal fixation device for reversibly fixing the operating aid 9 to another component of the medical imaging device 1, for example, an accessory rail of the patient table 4.

The operating aid 9 may also include a repositioning device 29 allowing to move the operating aid 9 between at least one usage position and at least one storage position. This will be further explained below.

As has already been explained with reference to FIG. 1, multiple operating aids 9 may be used by virtue of the barcode 22 allowing identification of the operating aids 9. Thus, the control device 10 or in particular the control unit 11 may automatically select suitable graphical elements projected to appear on the corresponding display surfaces 21.

Figure 5:
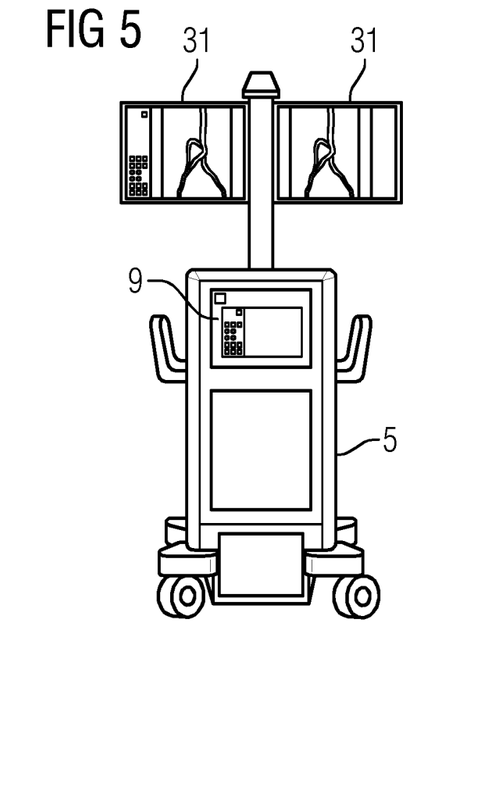
FIG. 5 depicts a first view of an exemplary display trolley.
Figure 6:
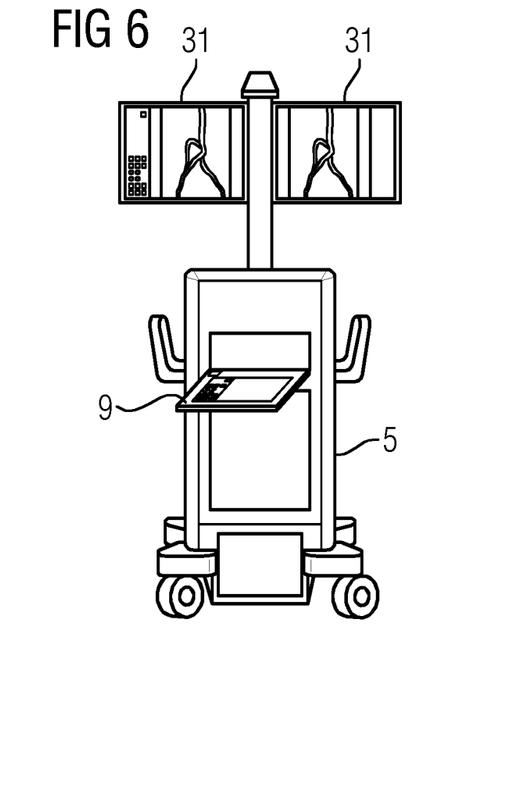
FIG. 6 depicts a second view of the display trolley.

FIG. 5 and FIG. 6 depict an operating aid 9 mounted to the display trolley 5, which in this case has two displays 31. The projection aid 9 is amounted using the repositioning device 29 and is thus shown in two different usage positions in FIGS. 5 and 6.

Figure 7:
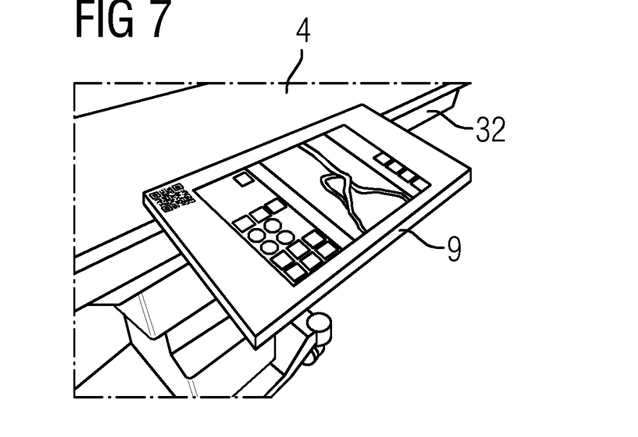
FIG. 7 depicts an example of an operating aid mounted to a patient table.

FIG. 7 illustrates mounting an operating aid 9 to an accessory rail 32 of the patient table 4.

Figure 8:
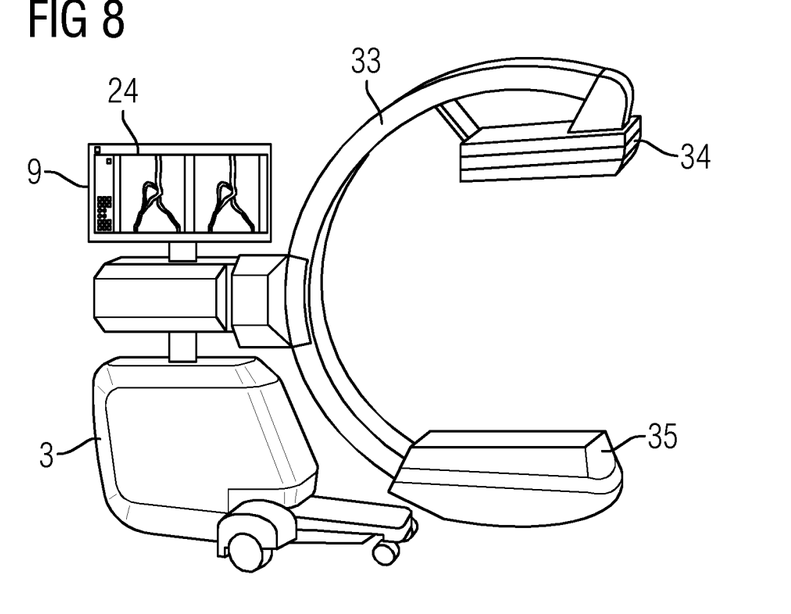
FIG. 8 depicts an example of a mobile image acquisition unit.

FIG. 8 depicts an operating aid 9 mounted to the image acquisition unit 3, which in this case includes a c-arm 33. An x-ray detector 34 and an x-ray source 35 are mounted to opposing ends of the c-arm 33. The operating aid 9 is in this case mounted to a support unit supporting the c-arm 33.

Figure 9:
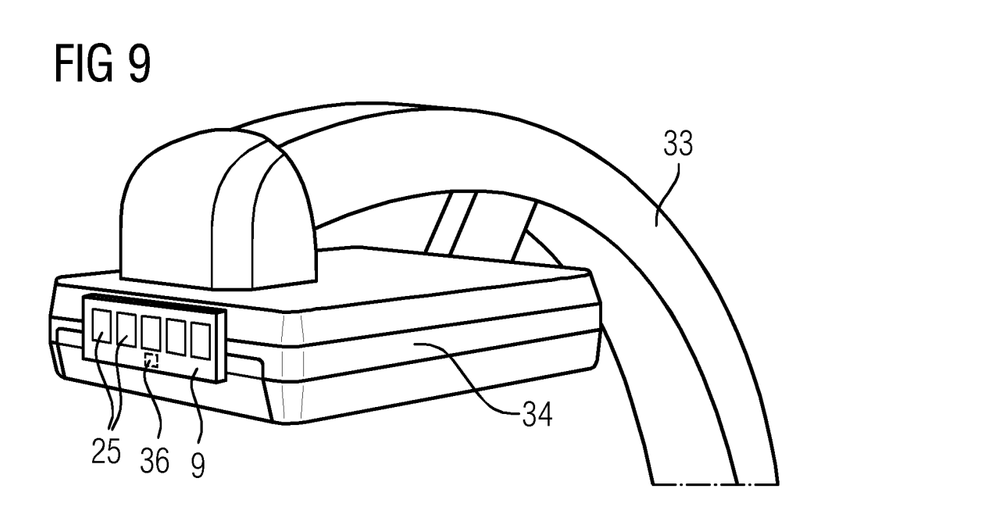
FIG. 9 depicts is a view of an exemplary x-ray detector.

FIG. 9 depicts a smaller operating aid 9 mounted to the x-ray detector 34.

It is noted that also safety relevant user commands may be received using projected virtual operating elements 25 if a confirmation signal caused by hardware is additionally received. For this purpose, the operating aid 9 or the component to which the operating aid 9 is mounted may include a pressure switch 36 (and/or capacitive sensor) as exemplarily shown in FIG. 9. If one of the virtual operating elements 25 and thus the operating aid 9 is pushed, the pressure switch 36 generates a confirmation signal. A safety relevant user command is only deemed as received if the associated interaction with the respective virtual operating element 25 as measured by the sensors 12 and the confirmation signal are both present.

If, as exemplarily described below, interactive operating elements 25 are used without an associated, tangible physical object, confirmation signals may also be generated using a confirmation aid 7 as shown in FIG. 1, which may be a hand or foot actuated switch. Interaction aids 8 may also include a confirmation switch 37, as indicated in FIG. 1, to be able to send confirmation signals. It should also be noted at this point that operating aids 9, confirmation aids 7 and interaction aids 8 may each include haptic feedback device 38 to give feedback to a user, for example, confirm detection and/or execution of a user command by vibrating the corresponding aid.

FIG. 10 again depicts the image acquisition unit 3 including the c-arm 33 with the x-ray detector 34 and the x-ray source 35. Sensor data of the sensors 12 of the smart glasses 6 may use pattern recognition algorithms to detect the "c" of the c-arm 33. Additionally, optical markers 39, in this case again QR codes, are attached to certain components, in this case the x-ray detector 34 and the x-ray source 35 to allow better detection and position/orientation measurement.

Figure 10:
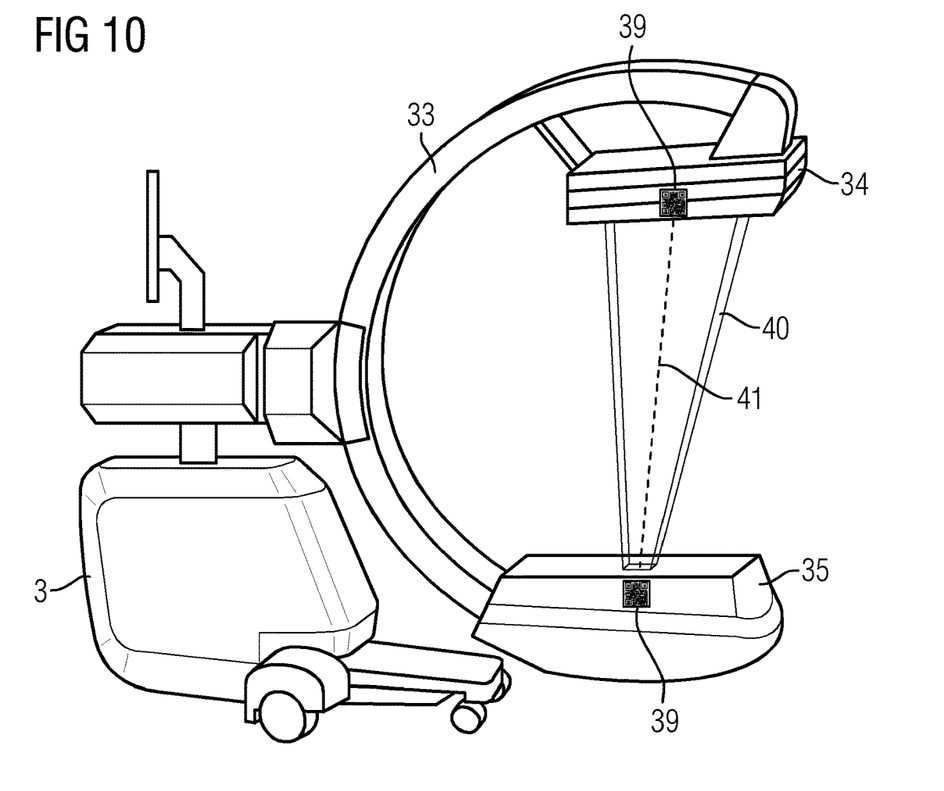
FIG. 10 depicts the mobile acquisition unit and its current field of view.

If the current positions of these components are known, the field of view 40 of the medical imaging device 1 may be calculated as well as the central beam 41.

Figure 11:
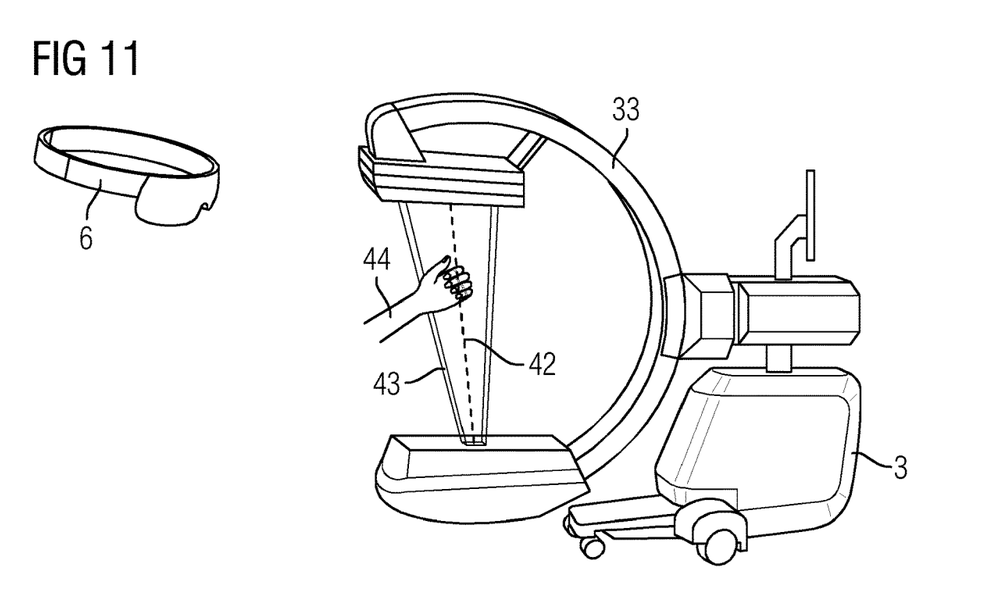
FIG. 11 depicts an example of a projected central beam as virtual operating element.

This information may also be displayed to the user using the smart glasses 6 and corresponding information elements, as shown in FIG. 11. Graphical element 42 corresponds to the central beam 41, graphical element 43 to the field of view 40. However, these graphical elements 42, 43 projected to match the locations of the real objects 40 and 41 are not only information elements, but also operating elements, as indicated by the hand 44 seemingly grabbing the graphical element 42 as a form of interaction. Grabbing the central beam graphical element 42 and moving it may result in movement of corresponding components to implement the new position and direction of the central beam 41 as input by interacting with the graphical element 42. In particular, the c-arm may be controlled to rotate, be raised or lowered, and/or be moved in a horizontal plane.

Figure 12:
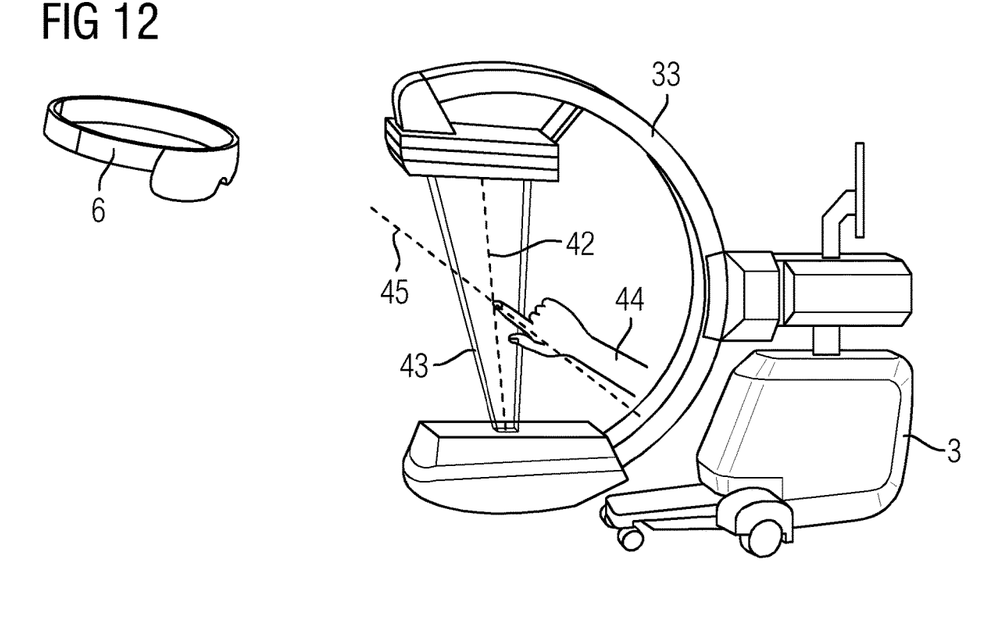
FIG. 12 depicts an exemplary drawing explaining choice of direction by a gesture.

FIG. 12 illustrates another possibility to define a new direction for the central beam 41 or pointing out a new region of interest by pointing to a certain region and/or in a certain direction, as indicated by the hand 44 and the graphical element 45.

Figure 13:
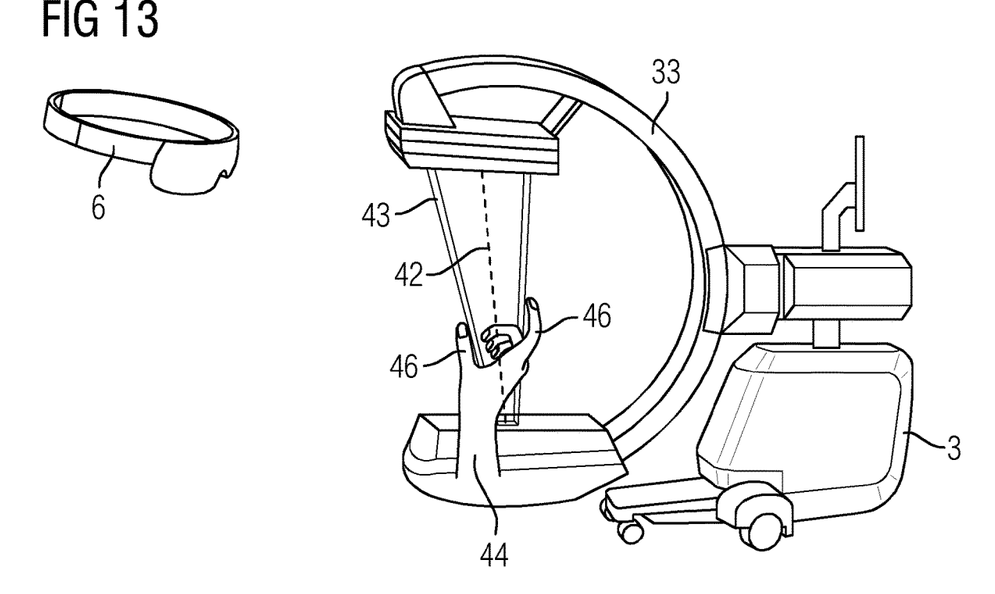
FIG. 13 depicts an exemplary drawing to explain controlling a diaphragm using a gesture.

FIG. 13 illustrates that also the graphical element 43 indicating the field of view 40 may be used as an interactive virtual operating element by positioning the hand 44 to grab the graphical element 43 and increase or decrease the distance between the fingers 46 to control collimation of the radiation field illustrated by graphical element 43. Because a fan-beam geometry is used here, the graphical element 43 has the form of a frustum of pyramid.

Figure 14:
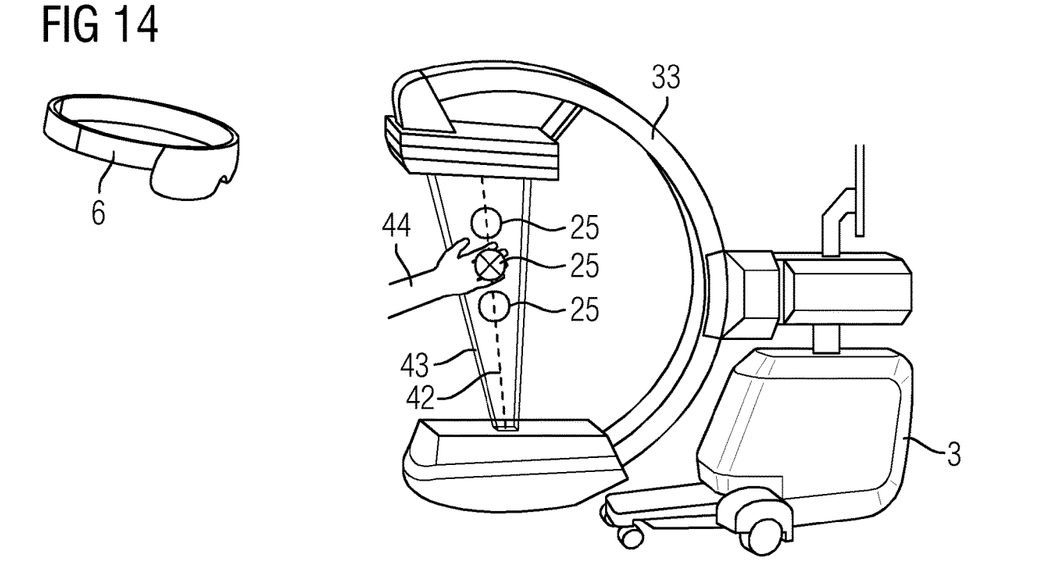
FIG. 14 depicts examples of additional virtual operating elements relating to the field of view.

As depicted in FIG. 14, additional interactive virtual operating elements 25 may be projected onto graphical element 43, in this case allowing to disable certain degrees of freedom of movement of the c-arm 33 or other components. For example, one of the virtual operating elements 25 may be associated with a horizontal movement of the c-arm 33, one virtual operating element 25 may be associated with an isocentric rotation of the c-arm and one virtual operating element 25 may limit movement of the c-arm to angular rotation.

It should be noted that further information may be displayed by coloring the graphical element 43, for example, to indicate a selected dose of radiation and the like.

For indicating directions or interacting with the central beam graphical element 42, use of an interaction aid 8 may be advantageous. The interaction aid 8 may then, for example, have the shape of a cylinder. This elongated shape allows clear definition of directions.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A medical imaging device comprising:
a user interface device configured to display information relevant to an imaging process to a user, receive user input relevant to the imaging process, or both display the information and receive the user input; and
at least one component controllable according to a user command entered using the user interface device,
wherein the user interface device comprises at least one pair of mixed reality smart glasses.

2. The medical imaging device of claim 1, wherein the medical imaging device is an x-ray device configured for intraprocedural imaging, and wherein a component of the at least one component comprises an imaging assembly having at least an x-ray source, an x-ray detector, and c-arm.

3. The medical imaging device of claim 2, wherein the x-ray device is a mobile x-ray device.

4. The medical imaging device of claim 1, wherein the smart glasses are configured to project at least one information element relating to the imaging process into a field of view of a user wearing the smart glasses.

5. The medical imaging device according to claim 4, wherein an information element of the at least one information element comprises a field of view of the medical imaging device displayed at an actual location of the medical imaging device.

6. The medical imaging device of claim 1, wherein the smart glasses are configured to project at least one interactive virtual operating element into a field of view of a user wearing the smart glasses,
wherein a control unit of the smart glasses is configured to derive the user command from interactions of the user with the virtual operating element as detected by at least one sensor of the smart glasses.

7. The medical imaging device of claim 6, wherein the smart glasses are configured to project at least one information element relating to the imaging process into a field of view of a user wearing the smart glasses, and
wherein the at least one information element comprises the interactive virtual operating element.

8. The medical imaging device of claim 6, wherein the user interface device further comprises an operating aid having a display surface,
wherein the control unit is configured to identify and locate the display surface and project the virtual operating element to appear on the display surface for the user wearing the smart glasses.

9. The medical imaging device of claim 8, wherein the operating aid has one or more of the following: a sterilizable surface, at least one fixation device, a device configured to interact with a mating fixation device and/or a standardized fixation device of the medical imaging device for reversibly fixing the operating aid to another component of the medical imaging device, or a repositioning device configured to move the operating aid between at least one usage position and at least one storage position.

10. The medical imaging device of claim 9, wherein the sterilizable surface is a surface comprising plastic, ceramics, metal, glass, or a combination thereof.

11. The medical imaging device of claim 9, wherein the fixation device is a magnetic fixation device.

12. The medical imaging device of claim 8, wherein, when using multiple different operating aids, the operating aid comprises at least one marker, bar code, or marker and bar code including or associated with identification information of the operating aid.

13. The medical imaging device of claim 8, wherein the operating aid has at least one tactile surface structure corresponding to a virtual operating element displayed at the position of the surface structure.

14. The medical imaging device of claim 8, wherein the operating aid or a component of the medical imaging device to which the operating aid is mounted comprises at least one pressure switch configured to indicate at least local pressing of the operating aid,
wherein user commands are grouped into safety relevant commands and other commands and the user interface device is configured to interpret an interaction with a virtual operating element projected on the display surface, which interaction corresponds to a safety relevant command, only as the corresponding user command when the pressure switch indicates pressing of the operating aid.

15. The medical imaging of claim 6, wherein the user interface device further comprises at least one interaction aid configured to be carried by the user and used for interacting with the virtual operating element.

16. The medical imaging device of claim 15, wherein the interaction aid comprises at least one confirmation switch configured to generate a confirmation signal required to enter a safety relevant command.

17. The medical imaging device of claim 8, wherein the user interface device further comprises at least one interaction aid configured to be carried by the user and used for interacting with the virtual operating element, and
wherein one or both of the operating aid and the interaction aid comprise a haptic feedback mechanism configured to generate feedback signals on user input.

18. The medical imaging device of claim 1, wherein the smart glasses comprise a holder for at least one vision-related surgery or imaging accessory.

19. The medical imaging device of claim 18, wherein the holder is configured to removably receive the at least one vision-related surgery or imaging accessory, or
wherein the holder comprises at least one positioning device for moving the accessory between at least one usage position in a field of view of a user or influencing the field of view of the user and a non-usage position.

20. The medical imaging device of claim 18, wherein the smart glasses comprise:
a control unit configured to project graphical elements into a field of view of a user wearing the smart glasses; and
at least one sensor configured to measure accessory sensor data describing one or more of a presence, a position, or a type of an accessory,
wherein the control unit is configured to control the display of the graphical elements depending on the accessory sensor data.

21. The medical imaging device of claim 20, wherein the graphical elements comprise virtual operating elements, information elements, or a combination thereof.

22. A method for supporting a person during an imaging process or a surgical intervention under image surveillance, the method comprising:
providing a user interface device comprising at least one pair of mixed reality smart glasses;
receiving user input via a user command relevant to an imaging process, wherein the user input is entered using the at least one pair of mixed reality smart glasses; and
displaying to a user, using the at least one pair of mixed reality smart glasses, information relevant to the imaging process.

* * * * *